(12) United States Patent
Tajima et al.

(10) Patent No.: US 11,141,576 B2
(45) Date of Patent: Oct. 12, 2021

(54) APPLICATOR FOR APPLYING A SHEET MEMBER TO SKIN

(71) Applicant: HISAMITSU PHARMACEUTICAL CO., INC., Tosu (JP)

(72) Inventors: Takuya Tajima, Tsukuba (JP); Naoki Yamamoto, Tsukuba (JP); Seiji Tokumoto, Tsukuba (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 238 days.

(21) Appl. No.: 16/471,290

(22) PCT Filed: Dec. 15, 2017

(86) PCT No.: PCT/JP2017/045156
§ 371 (c)(1),
(2) Date: Jun. 19, 2019

(87) PCT Pub. No.: WO2018/116990
PCT Pub. Date: Jun. 28, 2018

(65) Prior Publication Data
US 2019/0388668 A1    Dec. 26, 2019

(30) Foreign Application Priority Data
Dec. 20, 2016  (JP) .............................. JP2016-246295

(51) Int. Cl.
*A61M 37/00*      (2006.01)
(52) U.S. Cl.
CPC . *A61M 37/0015* (2013.01); *A61M 2037/0023* (2013.01)
(58) Field of Classification Search
CPC .......... A61M 2037/0023; A61M 37/00; A61M 37/0015; A61M 2037/0061
(Continued)

(56) References Cited

U.S. PATENT DOCUMENTS

2003/0180493 A1   9/2003  Hirashima et al.
2005/0096586 A1   5/2005  Trautman et al.
(Continued)

FOREIGN PATENT DOCUMENTS

CN      1901840 A    1/2007
CN    103687643 A    3/2014
(Continued)

OTHER PUBLICATIONS

Chinese Office Action dated Dec. 3, 2020 corresponding to application No. 201780078480.5.
(Continued)

*Primary Examiner* — Phillip A Gray
(74) *Attorney, Agent, or Firm* — Nath, Goldberg & Meyer; Joshua B. Goldberg

(57) ABSTRACT

An applicator of one embodiment is for applying a sheet member to skin. The applicator includes: a body including a bottom plate configured to face the skin and a bending portion provided to the bottom plate; a cap being movable along a slide direction substantially orthogonal to the bottom plate; and an elastic member configured to extend along the slide direction between the body and the cap. The elastic member applies, to the cap, elastic force that acts in a direction away from the bottom plate, the cap being movable toward the bottom plate against the elastic force. The bending portion bends the sheet member that has advanced thereto in a pressed state in which the cap has been moved toward the bottom plate, thereby applying the sheet member to the skin.

3 Claims, 12 Drawing Sheets

(58) Field of Classification Search
USPC .......................................................... 604/173
See application file for complete search history.

(56) References Cited

U.S. PATENT DOCUMENTS

| | | |
|---|---|---|
| 2005/0261631 A1 | 11/2005 | Clarke et al. |
| 2007/0106207 A1 | 5/2007 | Withey |
| 2015/0057604 A1 | 2/2015 | Arami et al. |
| 2015/0157840 A1 | 6/2015 | Kominami et al. |
| 2015/0258319 A1 | 9/2015 | Simmers |
| 2015/0290444 A1 | 10/2015 | Wirtanen et al. |
| 2016/0144160 A1 | 5/2016 | Yamamoto et al. |
| 2016/0354589 A1 | 12/2016 | Kobayashi et al. |
| 2016/0361527 A1 | 12/2016 | Jung et al. |
| 2017/0333690 A1* | 11/2017 | Ogura ............... A61M 37/0015 |

FOREIGN PATENT DOCUMENTS

| | | |
|---|---|---|
| CN | 105324148 A | 2/2016 |
| CN | 105517621 A | 4/2016 |
| EP | 1299147 | 1/2002 |
| JP | H3-198871 A | 8/1991 |
| JP | 7299147 A | 11/1995 |
| JP | 2005-118428 A | 5/2005 |
| JP | 2006523490 A | 10/2006 |
| JP | 2007-509706 A | 4/2007 |
| JP | 2011-147807 A | 8/2011 |
| JP | 2013-27492 A | 2/2013 |
| JP | 2014-200979 A | 10/2014 |
| TW | 201325643 A1 | 7/2013 |
| WO | 02/02177 A1 | 1/2002 |
| WO | 0202180 A2 | 1/2002 |
| WO | 2004091338 A1 | 10/2004 |
| WO | 2013/187392 A1 | 12/2013 |
| WO | 2014203910 A1 | 12/2014 |
| WO | 2016/088886 A1 | 6/2016 |
| WO | 2016/129184 A1 | 8/2016 |

OTHER PUBLICATIONS

International Preliminary Report on Patentability (IPRP) dated Jun. 25, 2019 issued in corresponding International Application No. PCT/JP2017/045156.
Notice of Allowance dated Jul. 21, 2020 corresponding to Japanese application No. P2018-557743.
Office Action dated Mar. 20, 2020 corresponding to Korean application No. 10-2018-7024447.
International Search Report dated Feb. 13, 2018 issued in corresponding International Application No. PCT/JP2017/045156.
Extended European Search Report dated Aug. 17, 2020 corresponding to application No. 17885207.5-1132.
Japanese Office Action dated Sep. 1, 2020 corresponding to application No. P2019-209852.
Office Action dated Jan. 9, 2020 corresponding to Taiwanese application No. 106144768.
Chinese Office Action dated May 19, 2021 corresponding to application No. 201780078480.5.

* cited by examiner

APPLICATOR FOR APPLYING A SHEET MEMBER TO SKIN

This is a National Phase Application filed under 35 U.S.C. 371 as a national stage of PCT/JP2017/045156, filed Dec. 15, 2017, an application claiming the benefit of Japanese Application No. 2016-246295, filed Dec. 20, 2016, the content of each of which is hereby incorporated by reference in its entirety.

TECHNICAL FIELD

One aspect of the present invention relates to an applicator used for assisting administration of an active ingredient.

BACKGROUND ART

Conventionally, sheet members for administering an active ingredient through skin have been known. Examples of the sheet members include a patch described in Patent Literature 1 below and a microneedle sheet described in Patent Literature 2 below.

CITATION LIST

Patent Literature

[Patent Literature 1] WO 2002/002177
[Patent Literature 2] WO 2013/187392

SUMMARY OF INVENTION

Technical Problem

A user sticks or attaches a sheet member to his/her skin by hand or using some auxiliary tool, thereby applying the sheet member to the skin. However, because force applied when such a sheet member is applied to skin varies depending on individual users, the condition for applying the sheet member accordingly varies among users, and consequently variations may occur in administration of an active ingredient. In view of this, it is desired to reduce variations in application of a sheet member to skin.

Solution to Problem

An applicator according to one aspect of the present invention is an applicator for applying a sheet member to skin, and includes: a body including a bottom plate configured to face the skin and a bending portion provided to the bottom plate; a cap being movable along a slide direction substantially orthogonal to the bottom plate; and an elastic member configured to extend along the slide direction between the body and the cap. The elastic member applies, to the cap, elastic force that acts in a direction away from the bottom plate, the cap being movable toward the bottom plate against the elastic force. The bending portion bends the sheet member that has advanced thereto in a pressed state in which the cap has been moved toward the bottom plate, thereby applying the sheet member to the skin.

In this aspect, the sheet member that has advanced toward the bending portion in the state (pressed state) in which the cap has been moved toward the bottom plate is bent by the bending portion and is then applied to the skin. By this mechanism, whoever uses this applicator, a certain or greater pressing force is applied to the sheet member when the sheet member is applied to the skin. Furthermore, because the cap and the elastic member are positioned above the bending portion along the direction (slide direction) substantially orthogonal to the bottom plate, whoever pushes the cap, the pressing force acts along this slide direction (direction substantially orthogonal to the skin). By these mechanisms, the direction and the magnitude of the pressing force can be easily maintained within a desired range, whereby variations in application of the sheet member to the skin can be reduced.

Advantageous Effects of Invention

According to the aspect of the present invention, variations in application of the sheet member to the skin can be reduced.

DESCRIPTION OF EMBODIMENTS

An embodiment of the present invention will now be described in detail with reference to the attached drawings. In the description of the drawings, like or equivalent elements are designated by like reference signs, and duplicated explanation is omitted.

An applicator is an auxiliary tool used when a sheet member for administering any active ingredient (e.g., a pharmaceutical substance) into a living body is applied to skin. The sheet member used together with the applicator and applied to the skin is not limited to a particular one, and examples thereof include a patch and a microneedle sheet. When using the applicator, a user can apply the sheet member to his/her skin with force that is more appropriate than when applying the sheet member directly by hand. The expression "the sheet member is applied to skin" at least means that the sheet member is in contact with the skin.

Figure 1:
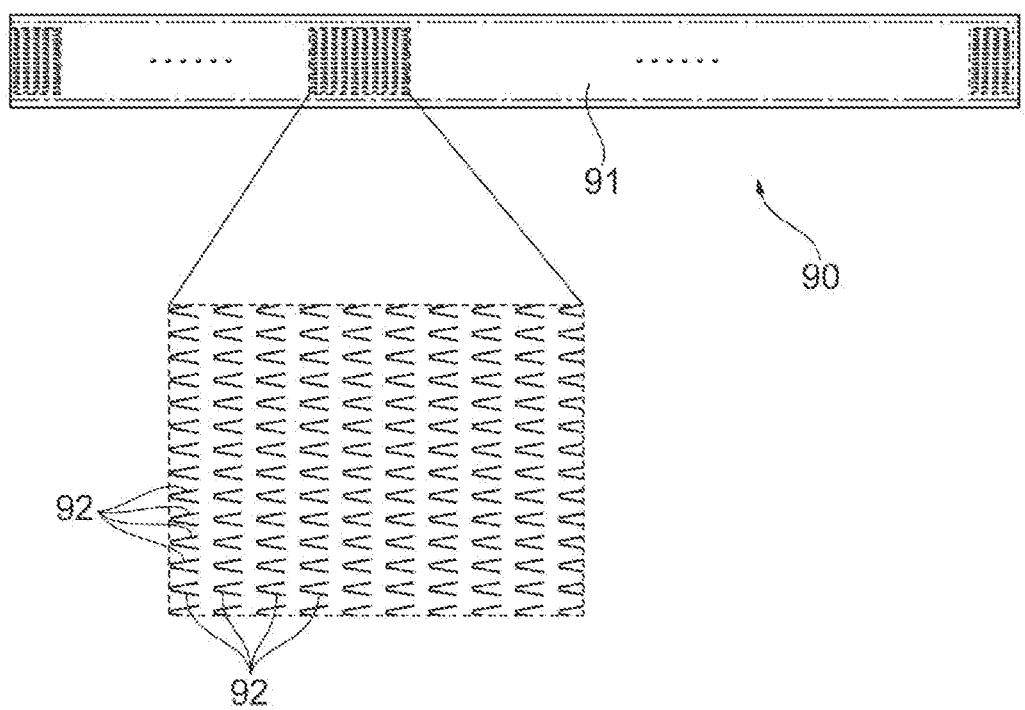
FIG. 1 is a plan view of a microneedle sheet used together with an applicator according to an embodiment.

In the present embodiment, a microneedle sheet will be described as one example of the sheet member. Referring to FIG. 1, the following describes this microneedle sheet 90 used together with the applicator according to the embodiment. FIG. 1 is a plan view of the microneedle sheet. As depicted in this diagram, the microneedle sheet 90 has a belt shape, and has a plurality of microneedles 92 formed on a main surface 91 of the sheet. In the present embodiment, the direction along its long side is called the longitudinal direction of the microneedle sheet 90, and the direction along its short side (direction orthogonal to the longitudinal direction) is called the width direction of the microneedle sheet 90. The direction orthogonal to both the longitudinal direction and the width direction is called the thickness direction of the microneedle sheet 90. The thickness (length along the thickness direction) of each microneedle 92 is the same as the thickness of the sheet. At the time when the microneedle sheet 90 is provided for use, each microneedle 92 does not rise from the main surface 91 of the sheet, and is extended substantially along the main surface 91. In other words, each microneedle 92 is in a state of lying along the main surface 91. The microneedles 92 are arranged so as to be aligned in both the longitudinal direction and the width direction (direction orthogonal to the longitudinal direction) of the sheet. The tips of all of the microneedles 92 are oriented toward one end of the sheet (to the left in FIG. 1). This can also be translated into that the angle formed by each microneedle 92 and the sheet is 0 degree or about 0 degree. The orientation of the tip of each microneedle 92 corresponds to the direction in which the microneedle sheet 90 advances when the microneedle sheet 90 is used. Herein, the orientation of some of the microneedles 92 may be different from the orientation of the others of the microneedles 92.

Material for the microneedle sheet 90 and the microneedles 92 is not limited to a particular one. For example, the microneedle sheet 90 and the microneedles 92 may be made of any of stainless steel, poly(ethylene terephthalate) (PET), water-soluble polymers, other metals, other resins, biodegradable material, ceramic, and bioabsorbable material. Alternatively, the microneedle sheet 90 and the microneedles 92 may be made of these materials in combination.

The microneedles 92 can be formed by etching. When the sheet is metal, the microneedles 92 can be formed by partially dissolving the sheet with a chemical solution. When the sheet is nonmetal, the microneedles 92 can be formed by partially cutting the sheet with a laser. In these cases, a void is formed around each microneedle 92. As a matter of course, the microneedles 92 may be formed by a method other than laser processing and etching. In all of these cases, the microneedles 92 do not have to be raised from the main surface 91 of the sheet in advance, and thus the microneedle sheet 90 can be produced easily at low cost.

As depicted in FIG. 1, in the present embodiment, each microneedle 92 has a triangular shape. However, the shape of the microneedle is not limited to a particular one. Although the sizes and orientations of the microneedles 92 and the distribution of the microneedles 92 in the microneedle sheet 90 are both uniform in the example in FIG. 1, both of them do not have to be uniform. When each microneedle 92 has a triangular shape, the angle of the tip portion thereof may be 10 degrees or larger, may be 20 degrees or larger, may be 150 degrees or smaller, or may be 120 degrees or smaller. When the microneedle sheet 90 is viewed along the longitudinal direction, a plurality of microneedles 92 may be formed on the sheet such that areas containing one or more microneedles 92 and areas containing no microneedles 92 are alternately arranged.

The dimensions of the microneedle sheet 90 are also not limited to particular ones. Specifically, the lower limit of thickness thereof may be either 5 micrometers or 20 micrometers, and the upper limit of the thickness may be either 1000 micrometers or 300 micrometers. The lower limit of length thereof may be either 0.1 centimeter or 1 centimeter, and the upper limit of the length may be 50 centimeters or 20 centimeters. The lower limit of width thereof may be either 0.1 centimeter or 1 centimeter, and the upper limit of the width may be either 60 centimeters or 30 centimeters. The lower limits of length and width of the microneedle sheet 90 are determined in consideration of the amount of an active ingredient to be administered, and the upper limits of length and width thereof are determined in consideration of the size of a living body.

Parameters for the microneedles 92 are also not limited to particular ones. Specifically, the lower limit of needle height thereof may be 10 micrometers or 100 micrometers, and the upper limit of the height may be 10000 micrometers, 1000 micrometers, or 500 micrometers. The lower limit of needle density thereof may be 0.05 needle/$cm^2$ or 1 needle/$cm^2$, and the upper limit of the density may be 10000 needles/$cm^2$ or 5000 needles/$cm^2$. The lower limit of the density is a value calculated based on the number of needles and the area that enable administration of 1 milligram of an active ingredient, and the upper limit of the density is a limit value determined in consideration of the shape of each needle.

Examples of a method considered for preparing an active ingredient to be applied to skin include: a method of causing the microneedle sheet 90 itself (more specifically, the microneedles 92 themselves) to contain the active ingredient in advance; a method of coating the microneedle sheet 90 itself with the active ingredient in advance; a method of applying the active ingredient onto skin before the skin is punctured with the microneedles 92; and a method of applying the active ingredient onto skin after the skin is punctured with the microneedles 92. If the microneedle sheet 90 is coated with the active ingredient in advance, coating liquid having a predetermined viscosity is preferably applied in uniform thickness to the entire sheet, and such application can be easily performed because the microneedles 92 lie along the main surface 91. This coating may be performed by using a principle of screen printing, or may be performed by using another method. When a biodegradable sheet or a sheet made with water-soluble polymer is used, the sheet itself can contain the active ingredient.

The microneedle sheet 90 may be provided in a form protected by a liner. Examples of material of the liner include plastics such as acrylic and PET. However, the material is not limited to a particular one, and the liner may be made with metal and another type of resin, for example. The microneedle sheet 90 is fixed or temporarily attached to one side of this liner with a tape or adhesive, for example.

In the microneedle sheet 90 before being bent by the applicator, the microneedles 92 are extended substantially along the main surface 91 of the sheet. Thus, unless the applicator is used, there is no need to worry that the microneedles 92 may come into contact with or be caught in another object (e.g., skin or clothes of a user). Consequently, safety from the microneedles 92 when being handled can be obtained. For example, the user can safely perform storage and transfer of the microneedle sheet 90, and preparation thereof immediately before using it.

Figure 2:
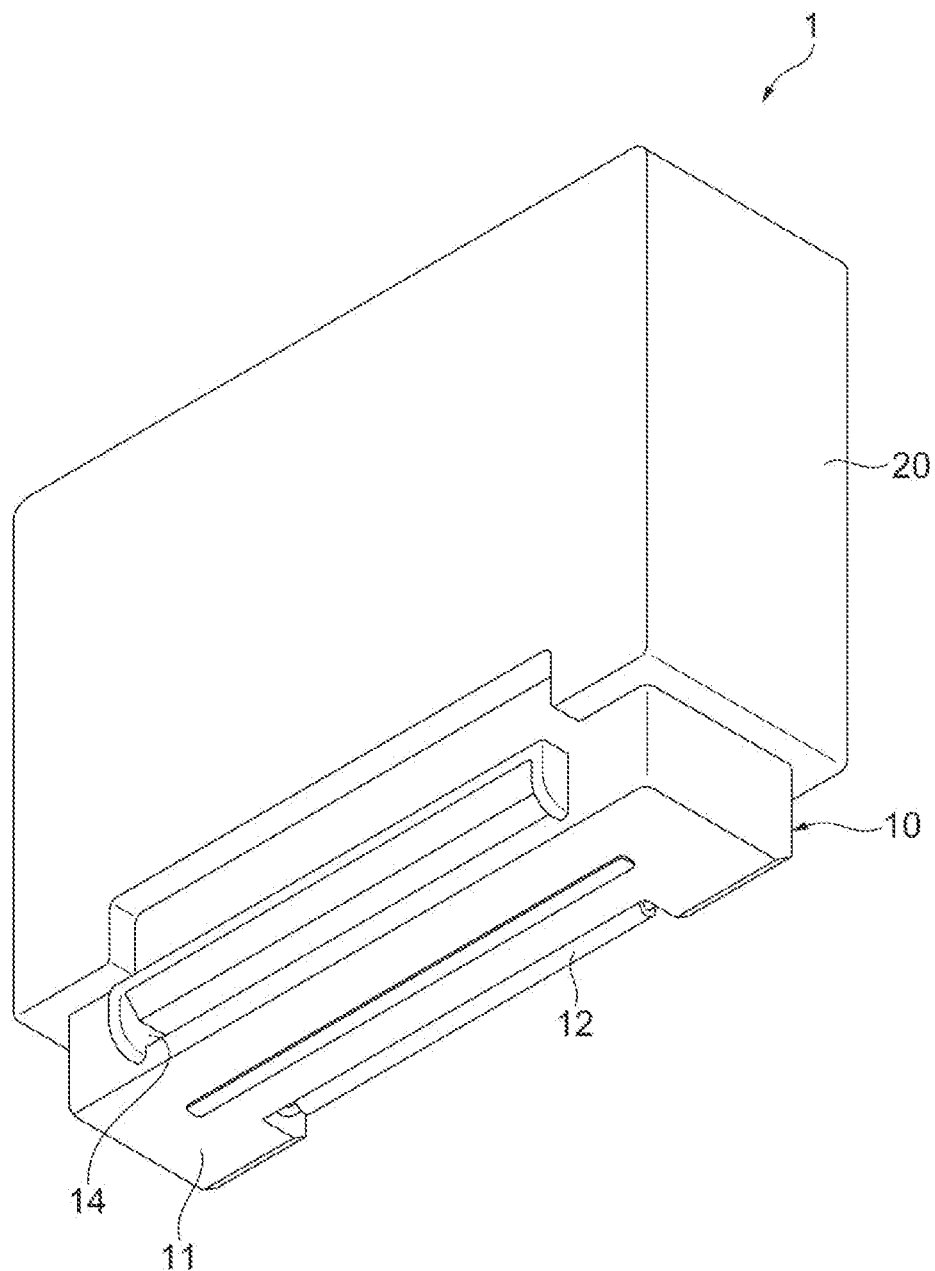
FIG. 2 is a perspective view of the applicator according to the embodiment when viewed from its bottom side.
Figure 3:
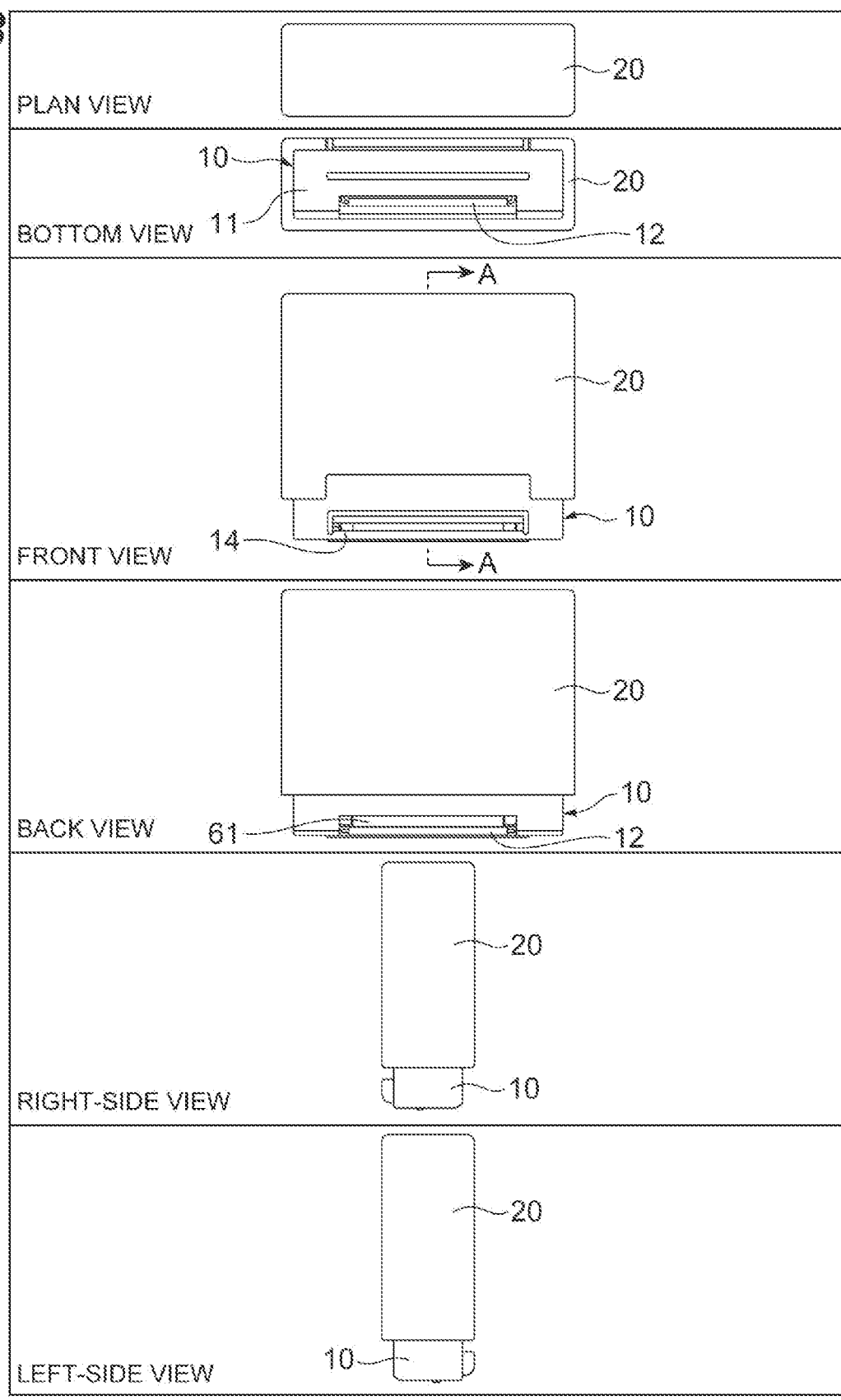
FIG. 3 is a six-sided view of the applicator according to the embodiment.
Figure 4:
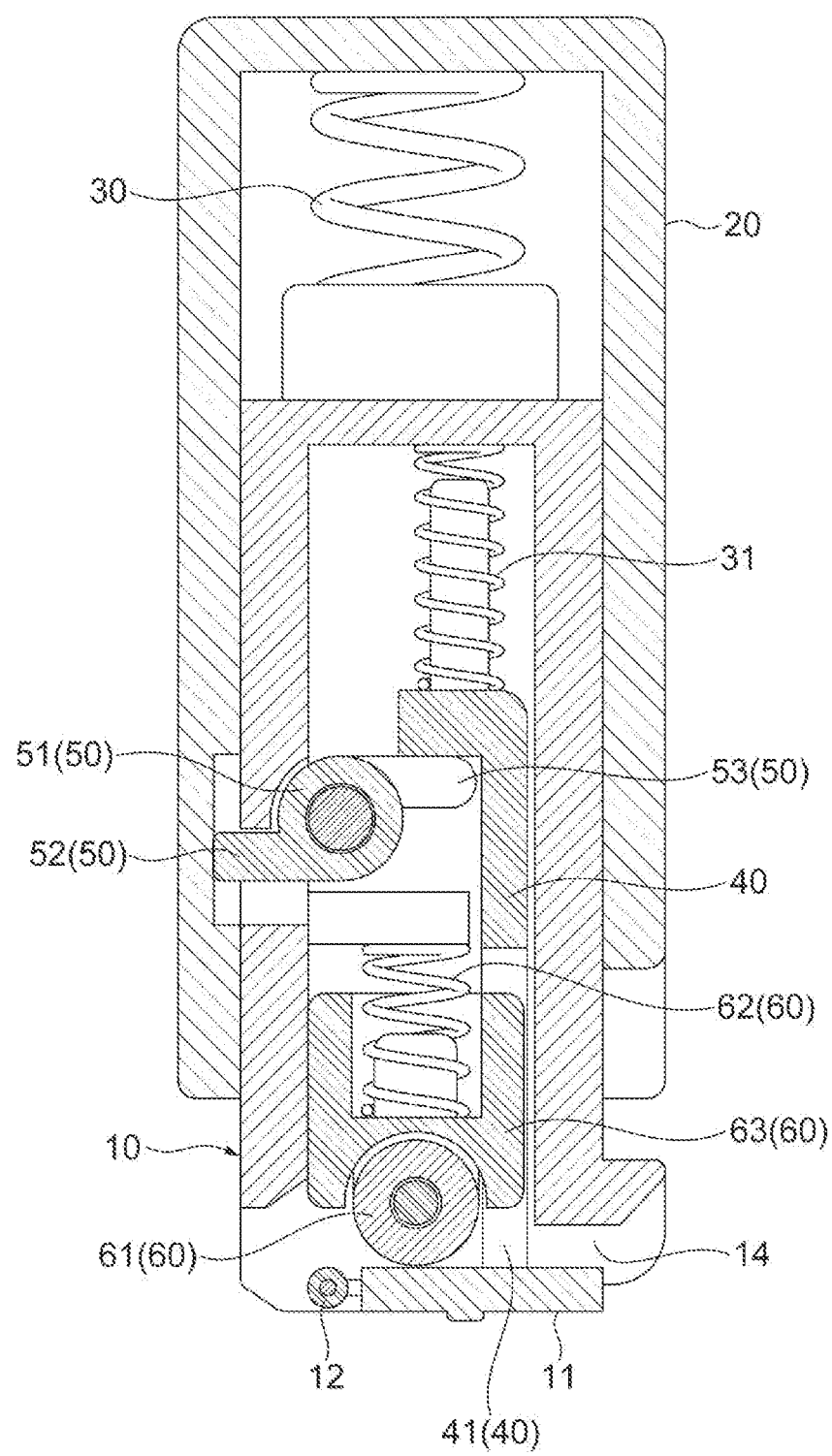
FIG. 4 is a sectional view of FIG. 3 (front view) taken along line A-A.
Figure 5:
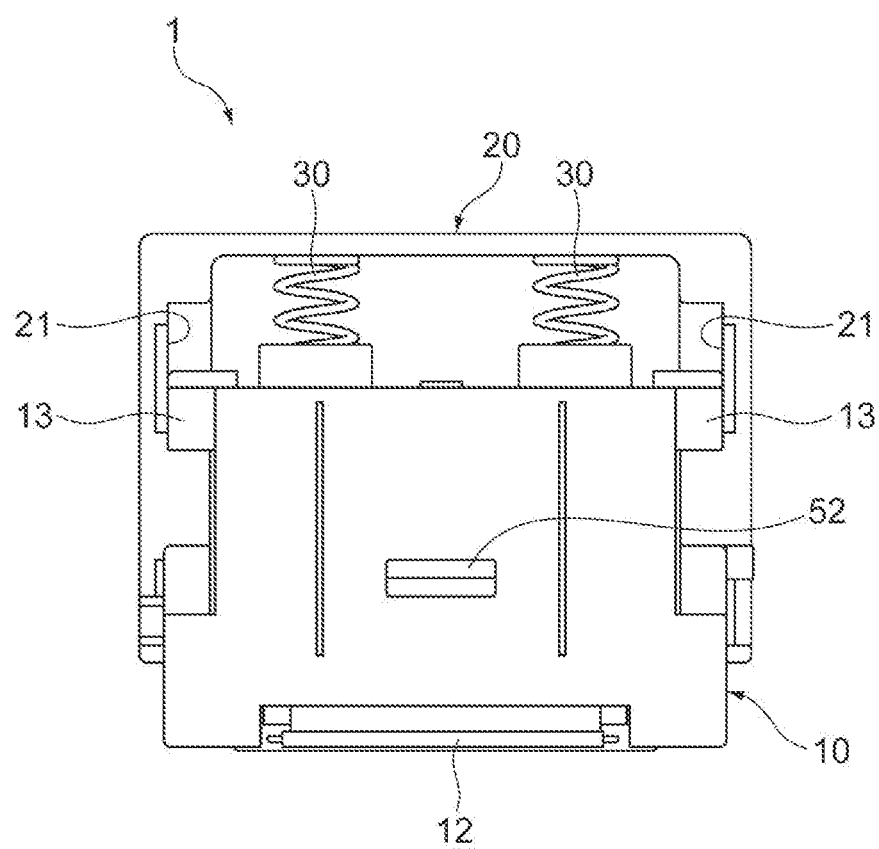
FIG. 5 is a diagram illustrating a back side of a body according to the embodiment.
Figure 6:
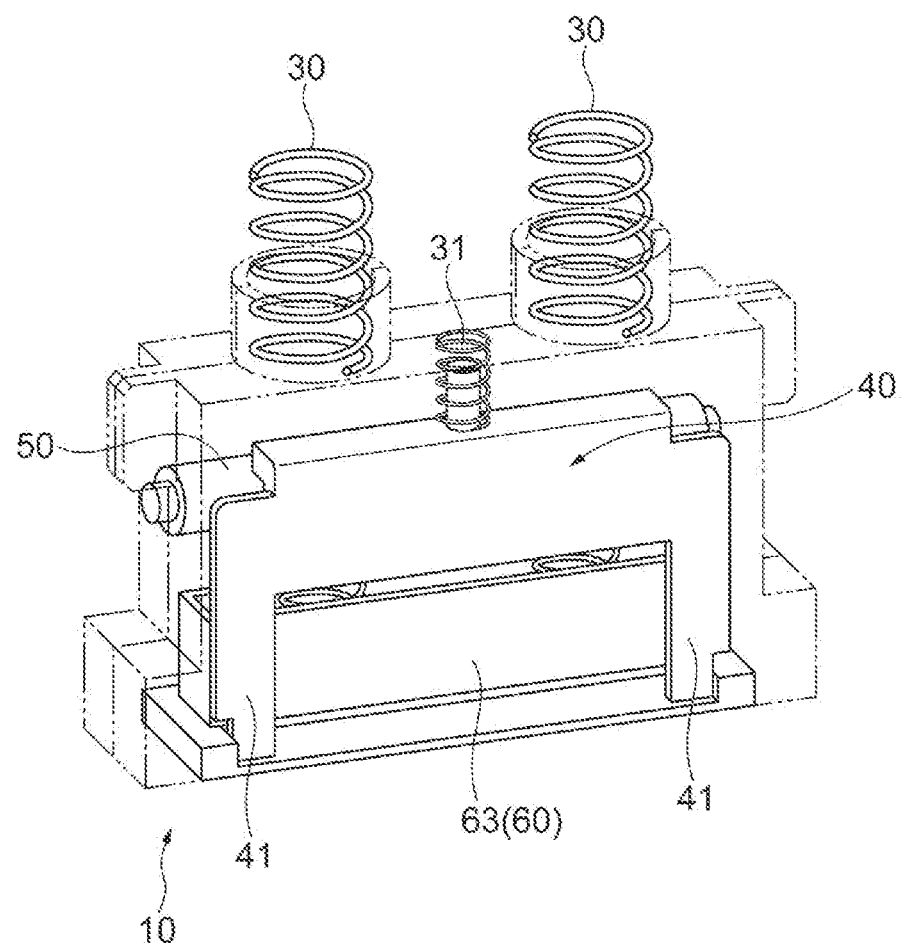
FIG. 6 is a perspective view illustrating an internal structure of the body according to the embodiment.
Figure 7:
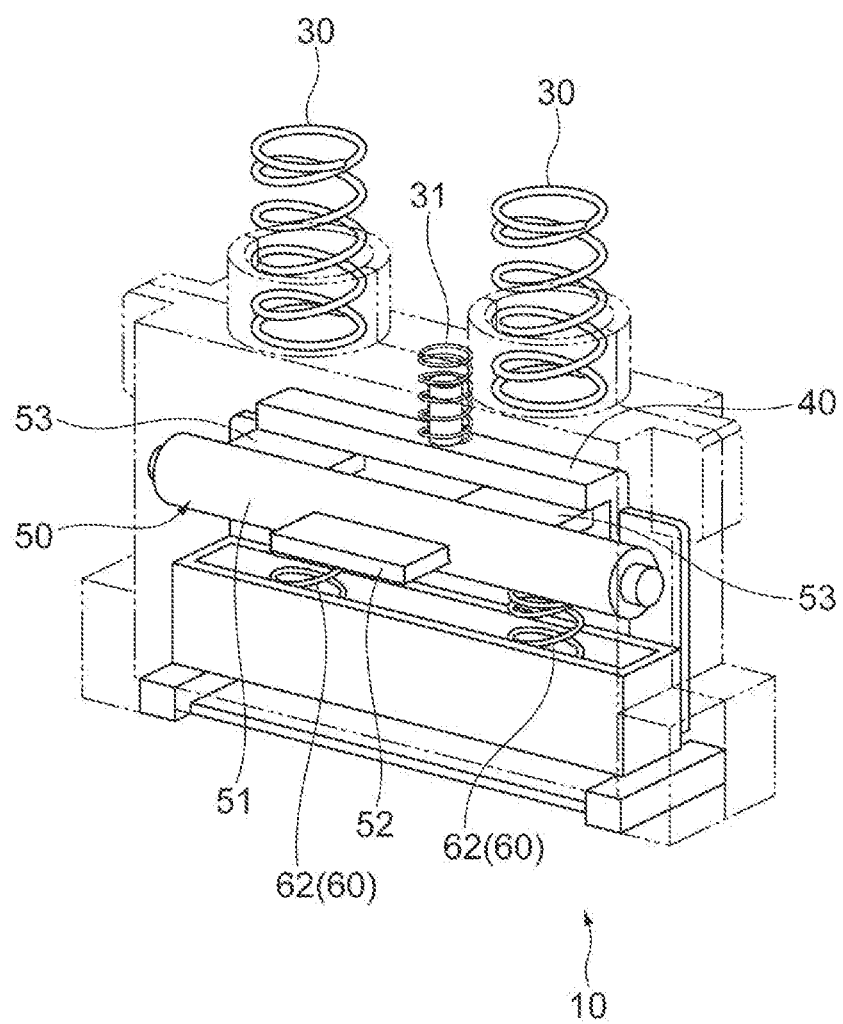
FIG. 7 is a perspective view illustrating the internal structure of the body according to the embodiment.
Figure 8:
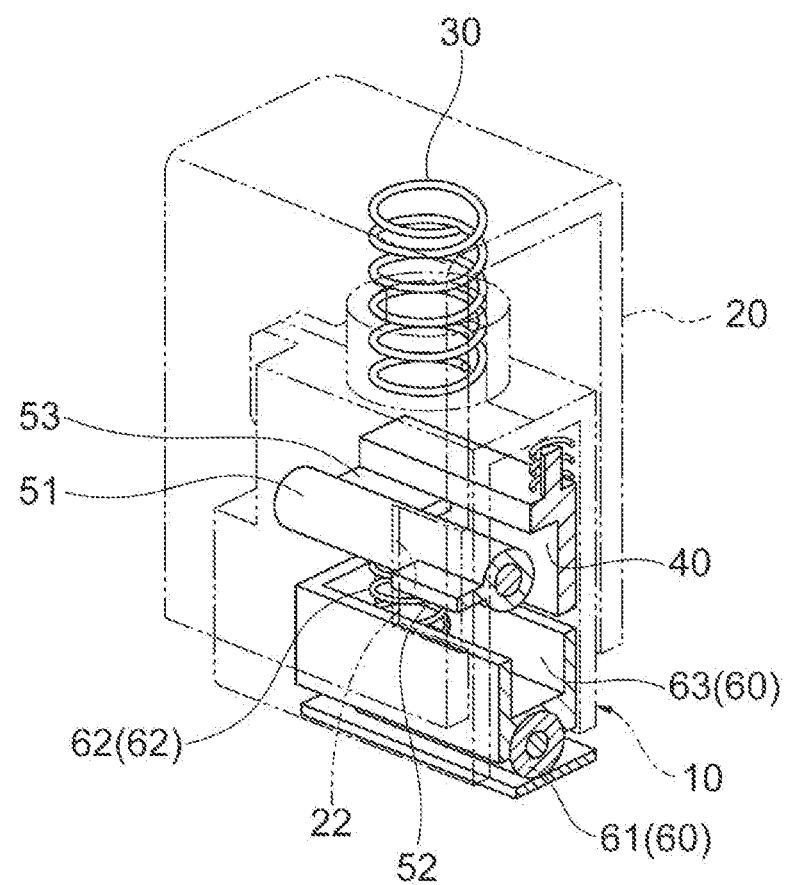
FIG. 8 is a sectional view illustrating the internal structure of the body according to the embodiment.

Referring to FIG. 2 to FIG. 8, the following describes a structure of the applicator 1. FIG. 2 is a perspective view of the applicator 1 when viewed from its bottom side. FIG. 3 is a six-sided view of the applicator 1. FIG. 4 is a sectional view of FIG. 3 (front view) taken along line A-A. FIG. 5 is a diagram illustrating a back side of a body, which indicates a state in which a back side of a cap is omitted. FIG. 6 and FIG. 7 are perspective views illustrating an internal structure of the body. FIG. 8 is a sectional view illustrating the internal structure of the body. In FIG. 8, a bending portion 12 described later is omitted.

The applicator 1 includes the body 10 in which the microneedle sheet 90 is set and the cap 20 provided in a manner covering the body 10. In the present embodiment, the body 10 and the cap 20 both have rectangular parallelepiped shapes that are vertically long and thin, and the applicator 1 as a whole accordingly has a rectangular parallelepiped shape that is vertically long and thin. The body 10 includes a bottom plate 11 having a planar shape and configured to face skin and the bending portion 12 provided to the bottom plate 11. The microneedle sheet 90 is set in the body 10, is moved forward on the bottom plate 11 by operation of the applicator 1 performed by the user, is bent by the bending portion 12, and is then applied to the skin. In the present embodiment, the side closer to the cap 20 is defined as the upper side of the applicator 1, and the side closer to the body 10 is defined as the lower side of the applicator 1. The side on which the microneedle sheet 90 enters the applicator 1 is defined as the front side of the applicator 1, and the side opposite thereto is defined as the rear side of the applicator 1. The direction orthogonal to both the vertical direction and the front-and-rear direction of the applicator is defined as the width direction of the applicator 1. The front-and-rear direction of the applicator 1 substantially corresponds to the longitudinal direction of the microneedle sheet 90, and the width direction of the applicator 1 substantially corresponds to the width direction of the microneedle sheet 90.

The cap 20 will be described first. The cap 20 can be moved along a direction (herein called "slide direction") orthogonal or substantially orthogonal to the bottom plate 11 of the body 10. Specifically, the cap 20 can be moved along the slide direction toward the bottom plate 11 or in a direction away from the bottom plate 11. Because the bottom plate 11 has a planar shape, it can be said that the slide direction orthogonal or substantially orthogonal to the bottom plate 11 is the same or substantially the same as the vertical direction of the applicator 1.

The above-described movement of the cap 20 with respect to the body 10 is controlled with at least one compression spring 30 configured to extend along the slide direction between the body 10 and the cap 20. In the present embodiment, the applicator 1 includes two compression springs 30. However, the number of compression springs 30 is not limited to this. In the present embodiment, one end of each compression spring 30 is attached to the upper surface of the body 10, and the other end thereof is attached to the ceiling of the cap 20. The compression spring 30 is one example of an elastic member configured to apply, to the cap 20, elastic force acting in the direction away from the bottom plate 11 thereby controlling movement of the cap 20 with respect to the body 10. In the present embodiment, the compression spring 30 is a linear coil spring. However, the type of the compression spring is not limited to this, and a nonlinear coil spring, for example, may be used instead. As described above, in the present embodiment, each compression spring 30 is provided so as to connect the upper surface of the body 10 and the ceiling of the cap 20. However, if the compression spring 30 can apply, to the cap 20, elastic force in the direction away from the bottom plate 11, the specific position where the compression spring 30 (elastic member) is attached is not limited to a particular one. For example, one end of the compression spring 30 may be attached to any location inside the body 10.

Unless the cap 20 is pressed by elastic force of the compression springs 30 toward the bottom plate 11 with a certain or greater force, the cap 20 is in a state of being located away from the bottom plate 11. In the present embodiment, a state in which the cap 20 has been moved toward the bottom plate 11 when external force is applied to the cap 20 is called "pressed state", and a state in which the cap 20 is not moved toward the bottom plate 11 is called "non-pressed state". It can be said that the pressed state is a state in which the cap 20 has been brought closer to the body 10, and the non-pressed state is a state in which the cap 20 is apart from the body 10. It can also be said that the non-pressed state is a natural state for the applicator 1 and the cap 20. The structure or elastic force of each compression spring 30 may be designed such that a certain or greater pressing force is applied to the microneedle sheet 90 (sheet member) when the microneedle sheet 90 (sheet member) is applied to skin.

The movable range of the cap 20 is controlled with grooves 21 formed in inner walls of the cap 20 and protruding portions 13 formed on side surfaces of the body 10. Each groove 21 is extended along the vertical direction (slide direction), and the corresponding protruding portion 13 extended in the width direction is fitted into the groove 21. The protruding portion 13 comes into contact with the lower end of the groove 21 in the non-pressed state, and comes into contact with the upper end of the groove 21 in the pressed state.

The following describes the body 10. Because the bottom plate 11 has a planar shape, the lower surface of the bottom plate, that is, the bottom surface of the applicator 1 can be considered to be a flat surface. Thus, it can be said that the slide direction is a direction orthogonal or substantially orthogonal to the bottom surface. On the lower surface of the bottom plate 11, a linear projection or dotted projections may be formed. By forming the bottom plate 11 such that part thereof projects toward skin, the microneedle sheet 90 (sheet member) is pressed against the skin by this projection, whereby the microneedle sheet 90 (sheet member) can be more reliably applied to the skin. However, this projection is not an indispensable element.

On the front side of the bottom plate 11, a slit 14 is formed that is extended in the width direction. This slit 14 is a hole through which the microneedle sheet 90 is inserted into the applicator 1.

On the rear side of the bottom plate 11, the bending portion 12 is provided. The bending portion 12 is a mechanical element configured to bend the microneedle sheet 90 that has advanced thereto in the pressed state to apply the microneedle sheet 90 to the skin. The bending portion 12 has a predetermined length along the width direction, and has a length that is substantially the same as the width of the microneedle sheet 90, for example. If the microneedles 92 can be raised from the main surface 91 by bending the microneedle sheet 90, the specific shape or structure of the bending portion 12 is not limited to a particular one. For example, the bending portion 12 may be formed with an elongated columnar member. In this case, the bending portion 12 may be rotatably provided in order to cause the microneedle sheet 90 to advance more smoothly, or does not have to rotate. When the bottom plate 11 is formed with a plate of a stainless steel (SUS plate) or resin, for example, an end portion of the plate may be caused to serve as the bending portion 12 by machining the end portion into a curved surface. The expression "the bending portion provided to the bottom plate" means that the bending portion is provided to the bottom plate itself or near the bottom plate.

Thus, each of the columnar member provided near the bottom plate and the end portion of the bottom plate is also one type of the bending portion provided to the bottom plate.

On the upper surface of the bottom plate 11, a passage (not depicted) connecting between the slit 14 and the bending portion 12 is formed. The microneedle sheet 90 that enters applicator 1 from the slit 14 passes through this passage to reach the bending portion 12.

The body 10 further includes a stopper 40, a camshaft 50, and a resistance portion 60. The stopper 40 is a mechanical element configured to stop the microneedle sheet 90 from advancing to the bending portion 12. The camshaft 50 is a mechanical element for controlling the stopper 40. The resistance portion 60 is a mechanism configured to apply resistance to the microneedle sheet 90 that is advancing to the bending portion 12. Both the stopper 40 and the resistance portion 60 are provided above the bottom plate 11, and the stopper 40 is positioned anteriorly to the resistance portion 60.

The stopper 40 is formed with a plate member having a C-shape (arch-like shape). Both ends of the stopper 40 in the width direction are leg portions 41 extended toward the bottom plate 11 along the slide direction. As depicted in FIG. 4 and FIG. 8, the upper end of the stopper 40 is formed so as to be bent in an L-shape toward inside (rear side) of the body 10.

The stopper 40 is attached inside the body 10 with at least one compression spring 31 configured to extend along the slide direction interposed therebetween. In the present embodiment, the applicator 1 includes one compression spring 31. However, the number of compression springs 31 is not limited to this. One end of the compression spring 31 is attached to the upper surface of the stopper 40, and the other end thereof is attached to the ceiling of the body 10. The compression spring 31 applies elastic force acting in a direction toward the bottom plate 11 to the stopper 40. The compression spring 31 is one example of an elastic member for controlling the stopper 40. In the present embodiment, the compression spring 31 is a linear coil spring. However, the type of the compression spring is not limited to this, and a nonlinear coil spring, for example, may be used instead.

By the elastic force of the compression spring 31, the stopper 40 is brought closer to the bottom plate 11 in the non-pressed state, and at this time, distal ends of the leg portions 41 are pressed against the upper surface of the bottom plate 11. Thus, in the non-pressed state, the microneedle sheet 90 is firmly nipped in the passage by the bottom plate 11 and the stopper 40, whereby the microneedle sheet 90 is stopped from advancing to the bending portion 12. The expression "to be stopped from advancing" herein means a state in which the microneedle sheet 90 (sheet member) cannot be caused to advance to the bending portion 12 unless the microneedle sheet 90 (sheet member) is forcefully pulled. The structure or elastic force of the compression spring 31 may be designed such that a pressing force substantially sufficient to prevent the microneedle sheet 90 (sheet member) from unintentionally advancing in the non-pressed state is applied to the microneedle sheet 90 (sheet member).

The camshaft 50 is provided that is extended along the width direction of the body 10. The camshaft 50 includes a first cam 52 formed on an outer peripheral surface of a rotating shaft 51 and a second cam 53 formed on the outer peripheral surface of the rotating shaft 51 and separated from the first cam 52 by about 180 degrees. The first cam 52 is fitted into a groove 22 formed in an inner wall of the cap 20, the groove 22 being extended along the vertical direction (slide direction) (see FIG. 8). The second cam 53 engages with the L-shaped upper end of the stopper 40, and more specifically, is in contact with a lower surface of this upper end. In the present embodiment, both the first cam 52 and the second cam 53 are claws protruding in the radial direction of the camshaft 50. However, if they can function as cams, the specific shapes of the first cam 52 and the second cam 53 are not limited to particular ones.

The camshaft 50 operates when the cap 20 is pushed toward the bottom plate 11. In the non-pressed state, the second cam 53 is in contact with the upper end of the stopper 40 pressed against the bottom plate 11. When the user presses the cap 20 and the cap 20 is accordingly moved toward the bottom plate 11 against elastic force of the compression spring 30 (i.e., when the applicator 1 is set into the pressed state), the upper end of the groove 22 comes into contact with the first cam 52 to push down the first cam 52. Accordingly, the camshaft 50 is rotated, and the second cam 53 positioned on the opposite side of the first cam 52 is moved upward along the circumferential direction. Because the second cam 53 engages with the upper end of the stopper 40, by this movement of the second cam 53, the stopper 40 is pulled up against the elastic force of the compression spring 31. In other words, the stopper 40 is moved in the direction away from the bottom plate 11. When the user stops pressing the cap 20 and the cap 20 is accordingly moved in the direction away from the bottom plate by the elastic force of the compression spring 30 (i.e., when the applicator 1 returns to the non-pressed state), pushing down of the first cam 52 by the groove 22 is released. Accordingly, the camshaft 50 is rotated reversely, whereby the second cam 53 is moved downward along the circumferential direction. Consequently, the stopper 40 is moved toward the bottom plate 11 by the elastic force of the compression spring 31.

The resistance portion 60 includes a roller 61 extended along the width direction and facing the bottom plate 11, at least one compression spring 62 disposed so as to extend in the slide direction above the roller 61, and a transmission portion 63 extended along the width direction and configured to transmit elastic force of the compression spring 62 to the roller 61. One end of each compression spring 62 is attached to an upper surface of the transmission portion 63, and the other end thereof is attached to a projecting portion (not depicted) inside the body 10.

In the present embodiment, the applicator 1 includes two compression springs 62. However, the number of the compression springs 62 is not limited to this. In the present embodiment, each compression spring 62 is a linear coil spring. However, the type of the compression spring is not limited to this, and a nonlinear coil, for example, may be used instead. The elastic force of the compression spring 62 is transmitted via the transmission portion 63 to the roller 61, whereby the roller 61 is pressed against the bottom plate 11. In other words, the compression spring 62 provides elastic force for pressing the roller 61 against the bottom plate 11.

The roller 61 is one example of a pressing member. The roller 61 may be rotatably provided in order to smoothly deliver the microneedle sheet 90 while applying resistance such as rolling friction and sliding friction to the microneedle sheet 90. However, rotation of the roller 61 is not indispensable. Because the roller 61 is pressed against the bottom plate 11 by the elastic force of the compression spring 62, the microneedle sheet 90 passing through the passage is nipped by the bottom plate 11 and the roller 61. The microneedle sheet 90 (sheet member) is nipped by using the elastic force in this manner, and thus the resistance applied to the microneedle sheet 90 (sheet member) can be kept constant.

If the elastic force of the compression spring 62 is excessively strong, it is difficult to insert the microneedle sheet 90 between the bottom plate 11 and the roller 61 and to cause the microneedle sheet 90 to advance toward the bending portion 12. If the elastic force is too weak, the microneedle sheet 90 may go slack, and accordingly a situation may occur in which the microneedle sheet 90 cannot be appropriately applied to skin (e.g., the microneedles 92 cannot be raised sufficiently). The structure or elastic force of the compression spring 62 may be designed so that the microneedle sheet 90 can be stretched without slack and the user can easily operate the applicator 1.

Material for forming the applicator 1 is not limited to a particular one. For example, examples of materials for the body 10 and the cap 20 include plastics such as acrylic. However, metal, another type of resin, and the like may be used instead. Material for the bending portion 12 may be metal, plastics such as acrylic, or another type of resin.

The dimensions of the applicator 1 may be determined based on any requirements. For example, the width of the applicator 1 may be determined based on the width of the microneedle sheet 90. The height and the entire length (length along the front-and-rear direction) of the applicator 1 may be determined in consideration of its operability.

Figure 9:
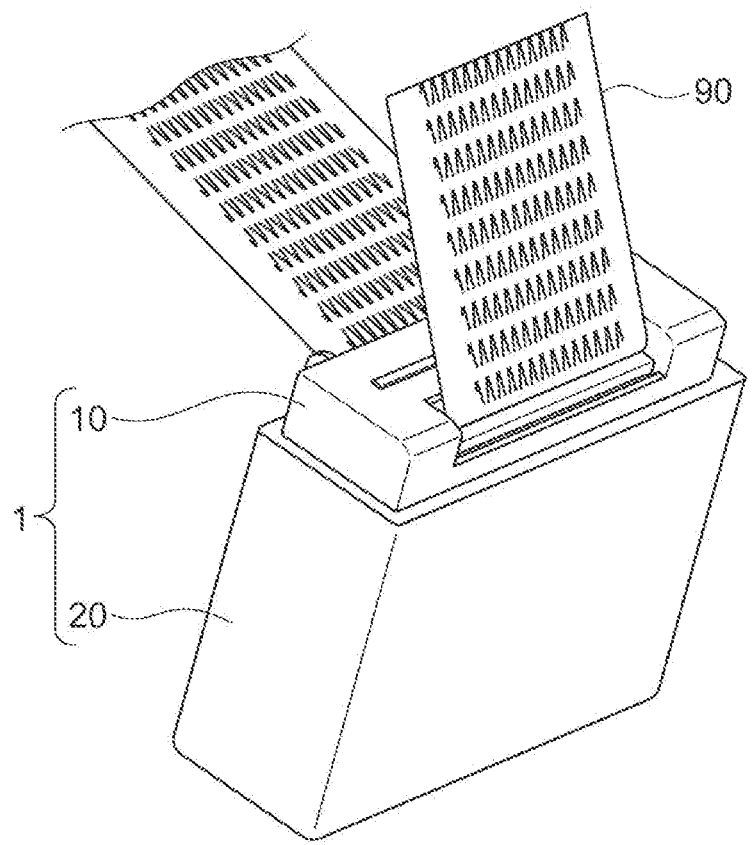
FIG. 9 is a diagram illustrating a method for using the applicator according to the embodiment.
Figure 10:
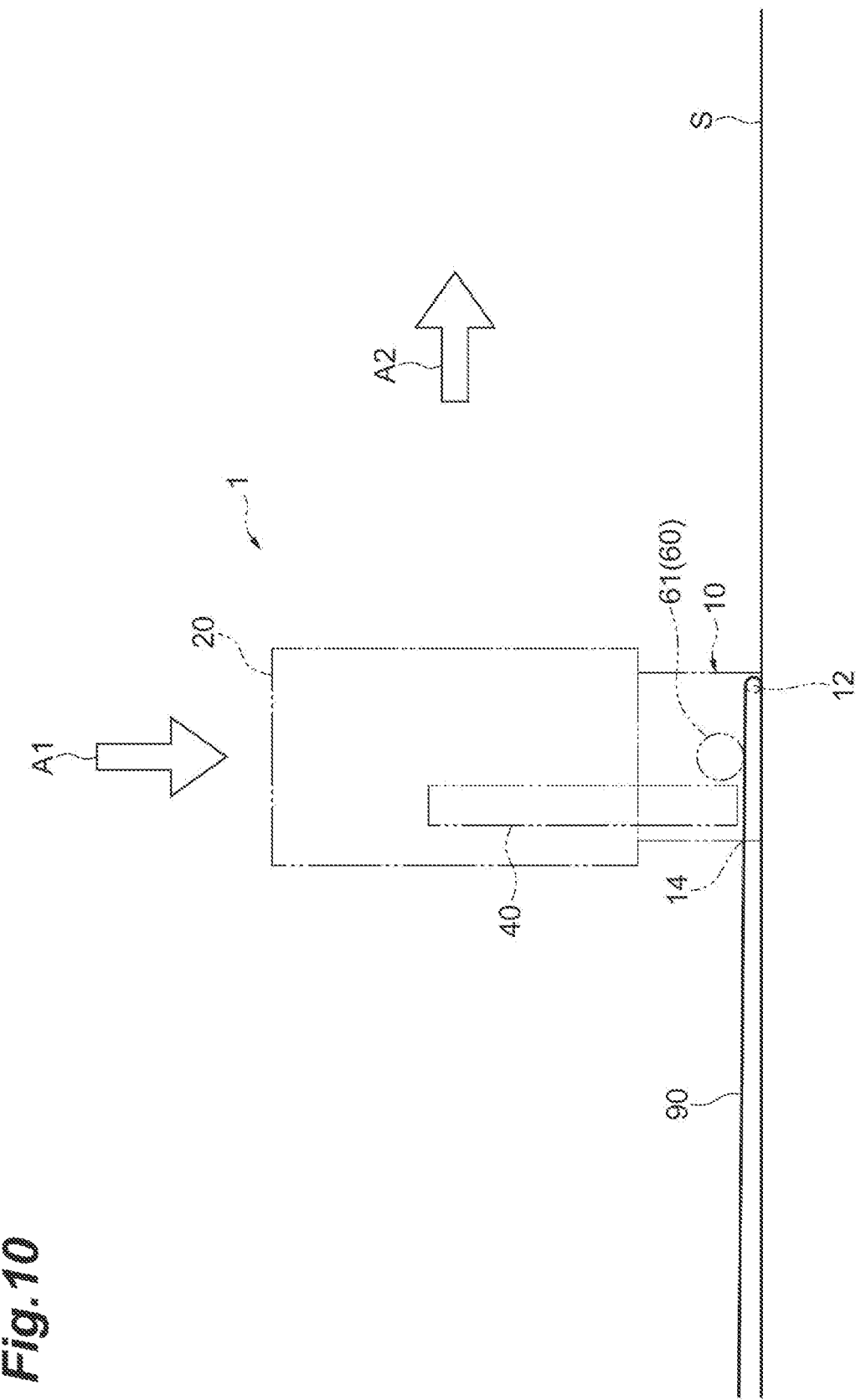
FIG. 10 is a diagram illustrating the method for using the applicator according to the embodiment.
Figure 11:
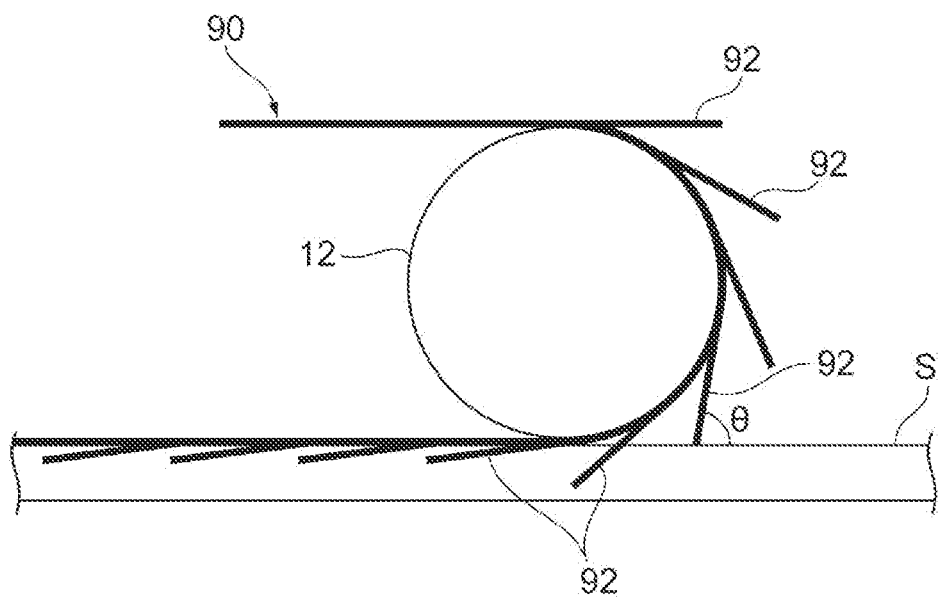
FIG. 11 is a diagram schematically illustrating a mode of puncture.

Referring to FIG. 9 to FIG. 11, the following describes methods for using the applicator 1 and the microneedle sheet 90. FIG. 9 and FIG. 10 are diagrams illustrating the method for using the applicator 1. FIG. 11 is a diagram schematically illustrating a mode of puncture. In FIG. 10, in order to depict how the microneedle sheet 90 is set in the applicator 1 in an easily understandable manner, the microneedle sheet 90 is illustrated with a continuous line, and the applicator 1 is illustrated with dashed and double-dotted lines.

To begin with, the user prepares the applicator 1 and the microneedle sheet 90, and sets the microneedle sheet 90 in the applicator 1 as depicted in FIG. 9. Specifically, the user inserts one end of the microneedle sheet 90 from the slit 14, and passes the microneedle sheet 90 therethrough until this one end comes out of the passage. The user then bends the microneedle sheet 90 near the bending portion 12. The direction of the tip of each microneedle 92 corresponds to the direction from the slit 14 toward the bending portion 12.

Subsequently, the user puts the applicator 1 on skin S (more specifically, in an area where an active ingredient is to be applied). When the applicator 1 has been simply put on the skin S, the applicator 1 is in the non-pressed state (natural state). In this non-pressed state, the stopper 40 is pressed against the bottom plate 11 by the compression spring 31, and thus the microneedle sheet 90 is stopped from advancing to the bending portion 12. The microneedle sheet 90 is also nipped in the passage by the bottom plate 11 and the roller 61.

Herein, in order to prevent the microneedle sheet 90 from being displaced on the skin S due to the subsequent operation of the applicator 1, adhesive may be applied to one end of the microneedle sheet 90 (end portion thereof that is brought into contact with the skin S from the beginning). Alternatively, the user may fix the one end of the microneedle sheet 90 to the skin S with his/her finger or an adhesive tape, for example.

As depicted in FIG. 10, while pushing the cap 20 toward the body 10, the user moves the applicator 1 rearward (toward the side where the bending portion 12 is positioned). In FIG. 10, the arrow A1 indicates a direction in which the cap 20 is pushed, that is, a direction in which the cap 20 is moved against the elastic force of the compression spring 30. The arrow A2 indicates a direction in which the applicator 1 is moved. The direction in which the cap 20 is pushed corresponds to the slide direction, and this direction also corresponds to the direction substantially orthogonal to the skin. Thus, the user pushes the cap 20 from substantially right above the skin.

When the cap 20 is pushed, the groove 22 pushes the first cam 52 toward the bottom plate 11, whereby the first cam 52 is lowered along the circumferential direction. Accordingly, the camshaft 50 is rotated, whereby the second cam 53 is raised along the circumferential direction. Consequently, the stopper 40 engaging with the second cam 53 is also raised, and thus a clearance is formed between the stopper 40 and the bottom plate 11. Because the stopper 40 is raised in this manner in the pressed state, during a period when the user is moving the applicator 1 rearward while pushing the cap 20, the microneedle sheet 90 advances in the passage without being stopped by the stopper 40. The microneedle sheet 90 enters the applicator 1 from the slit 14, and passes through the resistance portion 60 (more specifically, the roller 61) to reach the bending portion 12. Until having reached the bending portion 12, the microneedles 92 are in a state of being extended along the main surface 91 (i.e., a state of not rising from the main surface 91).

The compression spring 62 presses the roller 61 against the bottom plate 11 continuously even when the cap 20 is pushed and the stopper 40 is accordingly raised. Thus, during a period when the applicator 1 is being moved rearward in the pressed state, the resistance portion 60 nips the microneedle sheet 90 advancing to the bending portion 12 with the bottom plate 11 and the roller 61 thereby applying resistance to the microneedle sheet 90. Consequently, tension is applied to the microneedle sheet 90, whereby the microneedle sheet 90 is guided to the bending portion 12 without slack to be applied to the skin.

The microneedle sheet 90 that has advanced in the pressed state is bent (turned around) at the bending portion 12 by about 180 degrees. Accordingly, as depicted in FIG. 11, microneedles 92 located in a bent area are raised from the main surface 91, and the raised microneedles 92 are inserted into the skin S. The microneedles 92 that are raised between the applicator 1 and the skin S at once are those in one row along the width direction of the microneedle sheets 90. The bending portion 12 widens the angle formed between each microneedle 92 and the main surface 91, and this widened angle (angle formed between each raised microneedle 92 and the main surface 91) is larger than 0 degrees and smaller than 180 degrees as a matter of course. As depicted in FIG. 11, the puncture angle $\vartheta$ (angle formed between the microneedle 92 and the skin S) when the microneedle 92 raised from the main surface 91 is inserted into the skin is also larger than 0 degrees and smaller than 180 degrees. The lower limit of the puncture angle may be 20 degrees, 34 degrees, or 40 degrees, and the upper limit of this angle may be 160 degrees, 140 degrees, or 100 degrees. If the skin can be punctured with the microneedles 92, the angle by which the microneedle sheet 90 is bent at the bending portion 12 is not limited to 180 degrees. For example, this angle may be within a range of 135 to 180 degrees, and more specifically, may be 135 degrees, 150 degrees, 165 degrees, or 175 degrees.

When the user moves the applicator 1 by a desired distance, a plurality of microneedles 92 located in a range of this distance are inserted into the skin. Thus, the user can administer a desired amount of an active ingredient by adjusting the application area of the microneedle sheet 90. The user may remove the microneedle sheet 90 soon, or may apply the microneedle sheet 90 to the skin S continuously for a predetermined period of time.

As described above, the applicator 1 can be used also for application of a patch. The user sets a patch, with its adhesive-material layer facing upward, in the applicator 1 in the same manner as in the case of the microneedle sheet 90. The user then moves the applicator 1 rearward while pushing the cap 20 toward the bottom plate 11. By this operation, at the bending portion 12, the patch is bent such that the adhesive-material layer (active surface of the patch) faces outward of the arc of the bending portion, and the patch is stuck to the skin.

As described in the foregoing, an applicator according to one aspect of the present invention is an applicator for applying a sheet member to skin, and includes: a body including a bottom plate configured to face the skin and a bending portion provided to the bottom plate; a cap being movable along a slide direction substantially orthogonal to the bottom plate; and an elastic member configured to extend along the slide direction between the body and the cap. The elastic member applies, to the cap, elastic force that acts in a direction away from the bottom plate, the cap being movable toward the bottom plate against the elastic force. The bending portion bends the sheet member that has advanced thereto in a pressed state in which the cap has been moved toward the bottom plate, thereby applying the sheet member to the skin.

In this aspect, the sheet member that has advanced toward the bending portion in the state (pressed state) in which the cap has been moved toward the bottom plate is bent by the bending portion and is then applied to the skin. By this mechanism, whoever uses this applicator, a certain or greater pressing force is applied to the sheet member when the sheet member is applied to the skin. Furthermore, because the cap and the elastic member are positioned above the bending portion along the direction (slide direction) substantially orthogonal to the bottom plate, whoever pushes the cap, the pressing force acts along this slide direction (direction substantially orthogonal to the skin). By these mechanisms, the direction and the magnitude of the pressing force can be easily maintained within a desired range, whereby variations in application of the sheet member to the skin can be reduced. For example, when the sheet member is a patch, anyone who uses this applicator can securely apply an adhesive-material layer thereof to his/her skin while preventing the patch from wrinkling. When the sheet member is a microneedle sheet, anyone who uses this applicator can raise microneedles thereof from a main surface of the sheet, thereby securely inserting the microneedles into his/her skin.

In the applicator according to another aspect, the body may further include: a stopper being movable along the slide direction and capable of stopping the sheet member from advancing; and a camshaft configured to move the stopper toward the bottom plate to stop the sheet member from advancing when the cap is moved in the direction away from the bottom plate by the elastic force, and also configured to move the stopper in the direction away from the bottom plate to allow the sheet member to advance when the cap is moved toward the bottom plate against the elastic force. By using such a configuration in which the sheet member does not advance unless the cap is moved toward the bottom plate (i.e., unless the applicator is operated), the sheet member can be prevented from unintentionally advancing.

In the applicator according to another aspect, the body may further include a resistance portion configured to apply resistance to the sheet member that is advancing to the bending portion. Because tension is applied to the sheet member by applying the resistance to the sheet member that is advancing, the sheet member advances without slack, and consequently, the sheet member can be applied to the skin with a constant force.

In the applicator according to another aspect, the sheet member may be a microneedle sheet having a plurality of microneedles extended along a main surface of the sheet, and the bending portion may bend the microneedle sheet to raise the microneedles from the main surface such that the microneedles are inserted into the skin. In this case, variations in application of the microneedle sheet to the skin can be reduced, and anyone who uses this applicator can raise the microneedles from the main surface of the sheet, thereby securely inserting the microneedles into his/her skin. Furthermore, when this applicator is used, the microneedles are raised and then pushed into the skin without applying impact to the microneedle sheet, whereby the respective microneedles are inserted into the skin. Thus, an active ingredient can be administered, without giving fear, to a person to receive administration.

The present invention has been described above in detail based on the embodiment. However, the present invention is not limited to the embodiment above. In the present invention, various modifications may be made without departing from the gist thereof.

In the embodiment, springs have been described as elastic members. However, the elastic members are not limited to the springs. For example, part or all of each elastic member used as a component of the applicator may be an elastic body (e.g., rubber) other than a spring.

The stopper configured to stop the sheet member from advancing, the camshaft for controlling the stopper, and the resistance portion configured to apply resistance to the sheet member may all be omitted.

Figure 12:
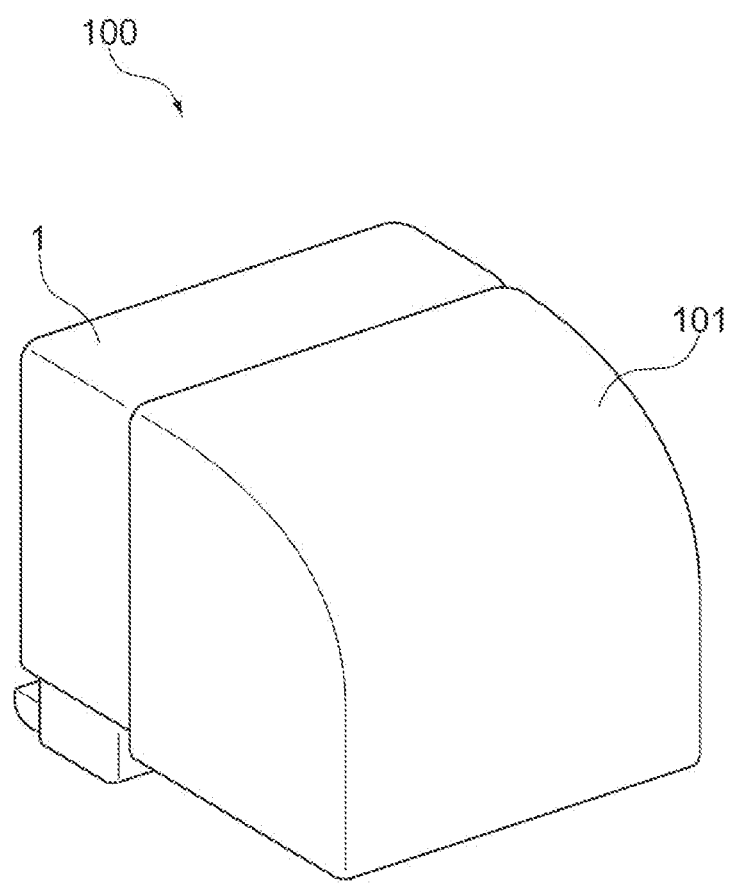
FIG. 12 is a perspective view illustrating an applicator according to a modification.

The shape of the applicator is not limited to that in the embodiment. FIG. 12 illustrates an applicator 100 according to a modification. This applicator 100 can be fabricated by attaching an expansion unit 101 to a rear side of the applicator 1 described above. The cross-section of the expansion unit 101 orthogonal to the width direction substantially has a fan shape in consideration of operability of the applicator 1. However, the shape of the expansion unit 101 is not limited to that in the example of FIG. 12. The shape of the applicator as a whole is also not limited to that in the example of FIG. 12.

As described above, the sheet member is not limited to a microneedle sheet. The applicator according to each aspect of the present invention may be used for other types of sheet members including a patch.

REFERENCE SIGNS LIST

1 . . . applicator, 10 . . . body, 20 . . . cap, 11 . . . bottom plate, 12 . . . bending portion, 14 . . . slit, 30 . . . compression spring (elastic member), 40 . . . stopper, 50 . . . camshaft, 52 . . . first cam, 53 . . . second cam, 60 . . . resistance portion, 90 . . . microneedle sheet (sheet member), 91 . . . main surface, 92 . . . microneedle, 100 . . . applicator, 101 . . . expansion unit

The invention claimed is:

1. An applicator for applying a sheet member to skin, comprising:
   a body including a bottom plate configured to face the skin and a bending portion provided to the bottom plate;
   a cap being movable along a slide direction substantially orthogonal to the bottom plate; and
   an elastic member configured to extend along the slide direction between the body and the cap, wherein
   the elastic member applies, to the cap, a first elastic force that acts in a direction away from the bottom plate, the cap being movable toward the bottom plate against the first elastic force, and
   the bending portion bends the sheet member that has advanced thereto in a pressed state in which the cap has been moved toward the bottom plate, thereby applying the sheet member to the skin, and
   the body further includes a resistance portion configured to apply resistance to the sheet member that is advancing to the bending portion, and
   the resistance portion includes a pressing member facing the bottom plate, and a compression spring transmitting, to the pressing member, a second elastic force for pressing the pressing member against the bottom plate, and
   the pressing member is pressed against the bottom plate by the second elastic force, and the resistance portion nips the sheet member with the pressing member and the bottom plate thereby applying the resistance to the sheet member.

2. The applicator according to claim 1, wherein the body further includes:
   a stopper being movable along the slide direction and capable of stopping the sheet member from advancing; and
   a camshaft configured to move the stopper toward the bottom plate to stop the sheet member from advancing when the cap is moved in the direction away from the bottom plate by the first elastic force, and also configured to move the stopper in the direction away from the bottom plate to allow the sheet member to advance when the cap is moved toward the bottom plate against the first elastic force.

3. The applicator according to claim 1, wherein the sheet member is a microneedle sheet having a plurality of microneedles extended along a main surface of the sheet, and the bending portion bends the microneedle sheet to raise the microneedles from the main surface such that the microneedles are inserted into the skin.

* * * * *